United States Patent [19]

Paparizos et al.

[11] Patent Number: 4,558,029

[45] Date of Patent: Dec. 10, 1985

[54] ANTIMONY-CONTAINING C₄ OXIDATION CATALYSTS

[75] Inventors: Christos Paparizos, Willowick; Robert S. Shout, Bedford Heights; Wilfrid G. Shaw, Lyndhurst, all of Ohio

[73] Assignee: The Standard Oil Company, Cleveland, Ohio

[21] Appl. No.: 690,823

[22] Filed: Jan. 11, 1985

Related U.S. Application Data

[63] Continuation of Ser. No. 417,773, Sep. 13, 1982, abandoned.

[51] Int. Cl.⁴ ............... B01J 27/19; B01J 27/198; C07C 51/16
[52] U.S. Cl. .................. 502/211; 502/209; 562/535
[58] Field of Search .................. 502/209, 211

[56] References Cited

U.S. PATENT DOCUMENTS

| | | | |
|---|---|---|---|
| 3,965,163 | 6/1976 | Oda et al. | 252/435 |
| 4,065,468 | 12/1977 | Grascelli et al. | 252/435 X |
| 4,093,558 | 6/1978 | Grascelli et al. | 252/435 X |
| 4,225,466 | 9/1980 | Wada et al. | 252/437 X |
| 4,238,359 | 12/1980 | Akeyama et al. | 562/534 X |
| 4,271,040 | 6/1981 | Khoobiar | 252/437 |
| 4,301,030 | 11/1981 | Shaw et al. | 252/437 X |
| 4,301,031 | 11/1981 | Shaw et al. | 252/437 X |
| 4,314,075 | 2/1982 | Shaw et al. | 252/437 X |
| 4,338,463 | 7/1982 | Shaw et al. | 252/437 X |
| 4,358,610 | 11/1982 | Pedersen et al. | 252/437 X |
| 4,374,757 | 2/1983 | Khoobiar | 252/435 X |
| 4,377,801 | 3/1983 | Khoobiar | 502/212 |
| 4,408,071 | 10/1983 | Pedersen et al. | 502/212 |

*Primary Examiner*—John Doll
*Assistant Examiner*—William G. Wright
*Attorney, Agent, or Firm*—Michael F. Esposito; John E. Miller, Jr.; Larry W. Evans

[57] ABSTRACT

Compositions of the empirical formula:

$$Mo_{12}P_{0.1-3}M_{0.1-3}Cu_{0.1-2}V_{0.1-2}Sb_{0.01-2}X_{0.01-2}Y_aO_x \quad (I)$$

where
  M is at least one of K, Rb and Cs;
  X is at least one of Ba, La, Ga, Al, Ag, Cd, Ti, Tl, Hg, Pb and Zn;
  Y is at least one of Fe, Co, Ni, Sr, Mn, In, Ta, Ge, S and Be when a>0;
  a is a number of 0 to about 2; and
  x is a number that satisfies the valance requirements of the other elements present, are excellent catalysts for the oxidation of oxygenated C₄ hydrocarbons, such as methacrolein, to methacrylic acid.

14 Claims, No Drawings

ANTIMONY-CONTAINING C4 OXIDATION CATALYSTS

This is a continuation of application Ser. No. 417,773 filed Sept. 13, 1982 now abandoned.

BACKGROUND OF THE INVENTION

1. Field of the Invention

This invention relates to catalysis. In one aspect, the invention relates to antimony-containing phosphomolybdic oxide catalysts while in another aspect, the invention relates to the use of these catalysts in the oxidation of oxygenated $C_4$ hydrocarbons to methacrylic acid.

2. Description of the Prior Art

The art is replete with various phosphomolybdic oxide catalysts useful for the oxidation of oxygenated $C_4$ hydrocarbons, such as methacrolein, isobutyraldehyde, t-butyl alcohol, etc. Representative of this art are U.S. Pat. Nos. 4,301,031; 4,301,030; 4,271,040 and 4,238,359. While the catalysts used in each of these teachings are all promoted phosphomolybdic oxide catalysts, they differ from one another primarily in the definition and combination of promoter elements. For example, the catalysts of U.S. Pat. No. 4,271,040 must contain at least one of cesium and calcium while the others can contain any alkali metal. As a further example, while the catalysts of these teachings can contain a combination of copper and vanadium, only U.S. Pat. Nos. 4,301,030 and 4,301,031 must contain this combination.

Although the catalysts of these references are generally quite good for their intended purpose, all are subject to improvement in methacrylic acid selectivity and catalyst life.

SUMMARY OF THE INVENTION

According to this invention, compositions of the empirical formula:

$$Mo_{12}P_{0.1-3}M_{0.1-3}Cu_{0.1-2}V_{0.1-2}Sb_{0.01-2}X_{0.01-2}Y_aO_x \qquad (I)$$

where
M is at least one of K, Rb and Cs;
X is at least one of Ba, La, Ga, Al, Ag, Cd, Ti, Tl, Hg, Pb and Zn;
Y is at least one of Fe, Co, Ni, Sr, Mn, In, Ta, Ge, S and Be when $a>0$;
a is a number of 0 to about 2; and
x is a number that satisfies the valance requirements of the other elements present,
are excellent catalysts for the oxidation of oxygenated $C_4$ hydrocarbons to methacrylic acid. These catalysts demonstrate both excellent selectivity for methacrylic acid and excellent catalyst life.

DETAILED DESCRIPTION OF THE INVENTION

Catalyst Composition:

The catalytic compositions of this invention, as evidenced from formula I, comprise at least eight elements, i.e. molybdenum, phosphorus, an alkali metal (M), copper, vanadium, antimony, at least one metal X, and oxygen all present in designated, proportional amounts. Preferably, the subscript value of phosphorus in formula I is about 0.5 to 1.75, of alkali metal (M) about 0.8–2, of copper about 0.1 to 0.8, of vanadium about 0.1 to 0.8, of antimony about 0.05 to 1, and of X about 0.02 to 0.5. The exact structure or element arrangement of these catalysts is not known but the metal and phosphorus components are present in the form of their oxides, acids, or oxide or oxyacid complexes. However, the compositions of formula I are known not to be a mere physical mixture of their components but rather unique oxide complexes where the individual components are chemically and/or physically bonded to one another.

Preferred catalysts are those where X is barium, mercury, thallium, zinc or lead and most preferred catalysts are those where X is barium, mercury or lead. In these preferred catalysts, M is typically rubidium or potassium. These catalysts can be further enhanced, at least in terms of activity and, in some cases catalyst life, by the addition of yet another component, here designated Y. When component Y is present ($a>0$), it is generally as iron, cobalt, tantalum or germanium.

As taught by formula I, certain of the components can be combinations of two or more elements, e.g. X can be a combination of barium and zinc. In such instances, the subscript value represents the sum of the elements (e.g. for X, the sum of barium and zinc is a number of about 0.01 to 2). Generally, M, X and Y each represent a single element.

Particularly preferred catalytic composition are eight element or component (including oxygen) catalysts where M is rubidium or potassium, X is barium, mercury or lead and a is zero.

The catalytic compositions of this invention can be used in either the 100% active form or in combination with a support (active or inert). In the latter case the composition can be coated on the support, intimately admixed with the support, or combined with the support in some other fashion. Suitable support materials include silica, titania, alumina, silica-alumina, zirconia, silicon carbide, boron, various phosphates, etc., with low surface area (about 1 $m^2/g$) silica-alumina a preferred support material. If a support is used, then the catalytic composition is generally present in an amount of at least about 20 weight percent, preferably in an amount of at least about 30 weight percent based upon the combined weight of the support and catalytic composition.

Catalyst Preparation:

The catalytic compositions here used can be prepared in any one of a number of different methods, the particular method employed being a matter of convenience. In one embodiment, the catalysts are prepared by mixing the appropriate catalyst ingredients in the proper proportion in an aqueous mixture, drying the resulting aqueous slurry with or without a reducing agent, and subsequently calcining the product. The ingredients can be added in any order during the preparation procedure but certain orders may be preferred, particularly the mixing of the metallic ingredients prior to the addition of the phosphorus (generally in the form of phosphoric acid). The ingredients employed can be the oxides, halides, nitrates, hydroxides, acetates or other salts of the particular metals or element added, and particularly preferred is the use of water soluble salts of the metal components. If a support is used, the materials comprising the support may be incorporated into the catalyst along with the other ingredients or the catalytic composition may be coated and/or impregnated onto or into a core. After the catalyst ingredients have been combined to form an aqueous slurry, the slurry is taken to dryness, the dried solid shaped to the desired form and then the shaped solid is heated in the presence of air, nitrogen, nitric oxide or a mixture of any two or more of these gases at temperatures between about 200° and about 450° C. This calcination can take place outside the catalytic reactor or an in situ activation can be utilized.

In another embodiment, the aqueous solution(s) of the catalyst components can be pH adjusted to some predetermined level and then aged prior to loading, assuming a support is used. Typically, the pH is adjusted to the range of 3–6.5. In yet another embodiment, the various catalyst components are dissolved or dispersed in nonaqueous media. Still other methods known in the art can be used to prepare the catalysts of this invention.

Methacrylic Acid Production:

The compositions of formula I are highly effective catalysts for the oxidation of oxygenated $C_4$ hydrocarbons to methacrylic acid. These oxygenated hydrocarbons include methacrolein, isobutyraldehyde, isobutyric acid and t-butyl alcohol. These catalytic compositions are used in the same manner as known catalytic compositions. These oxidation reactions are known reactions involving generally the contacting of gaseous oxygenated hydrocarbon with molecular oxygen at an elevated temperature. This particular embodiment of the invention is the use of these novel catalytic compositions in combination with the parameters of the known art processes.

Exemplary of these known processes is the contacting of gaseous methacrolein with molecular oxygen (typically supplied in the form of air), optionally in the presence of steam, at a temperature between about 275° and about 340° C. in the presence of a catalytic amount of the composition of formula I. The ratio of the reactants can vary widely with mole ratios of molecular oxygen to aldehyde of about 1 to 5 being typical. The amount of steam can also vary widely from a small amount generated in the reaction to 20 or more moles of steam per mole of aldehyde. Preferably if steam is used, then it is used in a concentration of about 1 to 10 moles of steam per mole of aldehyde. In certain embodiments of this invention, recycle gas (principally nitrogen, oxygen, carbon dioxide and carbon monoxide) can be used with or instead of steam.

These oxidation reactions can be conducted in a fixed-bed, fluid-bed or transfer-line reactor using atmospheric, superatmospheric or subatmospheric pressure. The contact time of reactants over the catalyst can vary from a fraction of a second to 20 or more seconds, the exact time depending upon the reaction conditions, such as catalyst composition, feed composition, temperature, pressure, reactor design, etc.

Although the catalytic compositions of this invention are particularly useful in the oxidation of oxygenated $C_4$ hydrocarbons to methacrylic acid, they are also useful in other oxidation reactions.

The following examples are illustrative of certain specific embodiments of this invention. Unless otherwise indicated, all parts and percentages are by weight.

SPECIFIC EMBODIMENTS

Catalyst Preparation:

The catalyst used in Example 1 was prepared by dissolving ammonium heptamolybdate (106.36 g) in distilled water (360 cc) with stirring and heating (30° C.). Potassium hydroxide (4.96 g) in distilled water (20 cc) was then added and after 15 minutes of additional heating and stirring, copper acetate (2.5 g in 40 cc of water) was added. With continued stirring and heating, ammonium metavanadate (1.46 g in 40 cc of hot water), barium acetate (1.28 g in 20 cc of water) and antimony pentoxide (1.78 g) was added to the mixture followed by concentrated hydrochloric acid (8 cc). The temperature of the mixture was then raised to 70° C. and stirring with heating continued for two additional hours. Phosphoric acid (7.7 g) was then added to the mixture and the mixture was then dropped to 30° C. and pH adjusted to about 5.5. The mixture was then evaporated to a thick paste and dried in an oven at 110° C. The catalyst powder was then coated onto ⅛ in. Alundum ® spheres (a low surface area silica-alumina) such that the coated catalyst contained about 33% by weight active catalyst.

The catalysts used in the remaining Examples, including the comparative Examples, were prepared by the same procedure used in preparing the catalyst of Example 1. This procedure was modified only to the extent necessary to effect the differences in the catalysts as described in their empirical formulae.

Process Procedure and Conditions:

The experiments were conducted in a 20 cc downward flow, fixed-bed reactor. All runs were performed in the same manner: one hour at 370° C. with air flow or three hours at 370° C. with nitrogen flow (no feed in both cases), followed by a temperature drop to the reaction temperature and introduction of the feed. After a stabilization period, samples were collected over 15 minutes at periodic intervals. Off-gas rate was measured with a soap-film meter and the off-gas composition was determined with the aid of a Carle 111 gas chromatograph. Each sample was diluted with distilled water to about 200 g. A weighed amount of valeric acid was used as an internal standard in a 20 g aliquot of the diluted solution. A one microliter sample was analyzed in a Varian Model 3700 gas chromatograph fitted with a flame ionization detector and a Polyester FF column. Total amounts of organic acid were determined by titrating 25 cc of the liquid with 0.1N sodium hydroxide. The splits between methacrylic, acrylic and acetic acid were determined by gas chromatographic analysis.

The process conditions were:
Pressure—atmospheric
Run Time—15 min
Contact Tine—3.1 sec
Feed Ratio—methacrolein:air:nitrogen:water=1:12:1.6:7.8

The results of the experiments made with the various catalysts are reported in Table I. Examples A–C are comparative examples.

TABLE I

| | | METHACROLEIN OXIDATION | | | | | |
|---|---|---|---|---|---|---|---|
| Ex. | Catalyst[1] | Temp. (°C.) | Time on Stream (hr) | MA Conv[2] | MAA Sel[3] | MAA PPC[4] | CO/ $CO_2$ | Carbon Balance |
| A | $Mo_{12} P_{1.33} K_{1.5} Cu_{0.25} V_{0.25} Ba_{0.1} O_x$ | 319 | 70 | 85.5 | 82 | 70.2 | 9.3 | 101.8 |
| 1 | $Mo_{12} P_{1.33} K_{1.5} Cu_{0.25} V_{0.25} Ba_{0.1} Sb_{0.38} O_x$ | 320 | 71 | 87.4 | 86.4 | 75.5 | 7.3 | 94.6 |

TABLE I-continued

METHACROLEIN OXIDATION

| Ex. | Catalyst[1] | Temp. (°C.) | Time on Stream (hr) | MA Conv[2] | MAA Sel[3] | MAA PPC[4] | CO/CO$_2$ | Carbon Balance |
|---|---|---|---|---|---|---|---|---|
| 2 | Mo$_{12}$P$_{1.33}$K$_{1.5}$Cu$_{0.25}$V$_{0.25}$Ba$_{0.1}$Sb$_{0.54}$O$_x$ | 327 | 90.1 | 86.5 | 86.6 | 74.9 | 7.0 | 98.3 |
| B | Mo$_{12}$P$_{1.33}$K$_{1.5}$Cu$_{0.25}$V$_{0.25}$Ba$_{0.1}$O$_x$ | 320 | 43 | 85.2 | 83.4 | 71.0 | 8.6 | 100.1 |
| 3 | Mo$_{12}$P$_{1.33}$K$_{1.5}$Cu$_{0.25}$V$_{0.25}$Ba$_{0.1}$Sb$_{0.22}$O$_x$ | 320 | 72.5 | 88.4 | 85.0 | 75.2 | 7.4 | 101.8 |
| 4 | Mo$_{12}$P$_{1.33}$K$_{1.5}$Cu$_{0.25}$V$_{0.25}$Ba$_{0.1}$Sb$_{0.5}$O$_x$ | 320 | 70.3 | 88.5 | 85.3 | 75.4 | 7.9 | 100.3 |
| C | Mo$_{12}$P$_{1.33}$K$_{1.5}$Cu$_{0.25}$V$_{0.25}$Sb$_{0.38}$O$_x$ | 320 | 69.8 | 75.8 | 88.0 | 66.7 | 5.0 | 99.3 |
|   |   | 320 | 72.6 | 79.0 | 88.7 | 70.2 | 5.2 | 96.9 |
| 5 | Mo$_{12}$P$_{1.33}$Cs$_{1.5}$Cu$_{0.25}$V$_{0.25}$Ba$_{0.1}$Sb$_{0.38}$O$_x$ | 320 | 75.9 | 87.8 | 85.5 | 75.0 | 7.8 | 101.9 |

[1]Catalysts A, C, 1, 2 and 5 were calcined at 370° C. for 3 hours under N$_2$. Catalysts B, 3 and 4 were calcined at 370° C. for 1 hour under air.

[2]Methacrolein conversion = $\frac{\text{Moles of MA reacted} \times 100}{\text{Moles of MA fed}}$

[3]Methacrylic acid selectivity = $\frac{\text{Moles of MAA produced} \times 100}{\text{Moles of MA reacted}}$

[4]Per pass conversion to methacrylic acid = MA conversion × MAA selectivity.

A comparison of the data of comparative Example A and Examples 1 and 2, each calcined at 370° C. for three hours under nitrogen, demonstrates that those catalysts having antimony as a component convert more methacrolein and are more selective to methacrylic acid than the catalysts without antimony as a component. This comparison holds true for catalysts calcined under different conditions, i.e. the catalysts of comparative Example B and Examples 3 and 4 were calcined for one hour at 370° C. under air. A comparison of the data of comparative Example C (both runs) and Example 5 demonstrate the positive contribution of the X component (here barium) to the catalysts of this invention.

Although the invention has been described in considerable detail through the preceding examples, these examples are for the purpose of illustration only and those skilled in the art understand that variations and modifications can be made without departing from the spirit and scope of the appended claims.

What is claimed is:

1. A catalytic composition of the empirical formula:

$$Mo_{12}P_{0.1-3}M_{0.1-3}Cu_{0.1-2}V_{0.1-2}Sb_{0.01-2}X_{0.01-2}Y_aO_x$$

where
M is at least one of K, Rb and Cs;
X is at least one of Ba, Hg, and Pb;
Y is at least one of Fe, Co, Ni, Sr, Mn, In, Ta, Ge, S and Be when a>0;
a is a number from 0 to about 2; and
X is a number that satisfies the valence requirements of the other elements.

2. The composition of claim 1 where M is potassium or rubidium.

3. The composition of claim 2 where a is greater than zero.

4. The composition of claim 3 where Y is iron, cobalt, tantalum or germanium.

5. The composition of claim 2 where a is zero.

6. The composition of claim 5 where the subscript value of phosphorus in formula I is about 0.5 to 1.75, of M about 0.8 to 2, of copper about 0.1 to 0.8, of vanadium about 0.1 to 0.8, of antimony about 0.05 to 1, and of X about 0.02 to 0.5.

7. The composition of claim 6 which is essentially 100% active.

8. The composition of claim 6 diluted with a support.

9. The composition of claim 8 where the support is a low surface area silica-alumina.

10. The composition of claim 8 where the catalytic composition is coated onto a low surface area silica-alumina support.

11. The composition of claim 10 where X is lead.

12. The composition of claim 10 where X is barium.

13. The composition of claim 10 where Y is germanium.

14. The composition of claim 10 wherein X is mercury.

* * * * *